United States Patent
Krumrey et al.

(10) Patent No.: US 9,856,202 B2
(45) Date of Patent: Jan. 2, 2018

(54) PROCESS FOR THE RECOVERY OF CARBOXYLIC ACID AND WOOD TREATMENT PROCESS

(71) Applicant: SOLVAY ACETOW GmbH, Freiburg (DE)

(72) Inventors: Thomas Krumrey, Teningen (DE); Andreas Hummel, Freiburg (DE)

(73) Assignee: SOLVAY ACETOW GMBH, Freiburg Im Breisgau (DE)

( * ) Notice: Subject to any disclaimer, the term of this patent is extended or adjusted under 35 U.S.C. 154(b) by 0 days.

(21) Appl. No.: 15/309,590

(22) PCT Filed: May 6, 2015

(86) PCT No.: PCT/EP2015/059921
§ 371 (c)(1),
(2) Date: Nov. 8, 2016

(87) PCT Pub. No.: WO2015/169833
PCT Pub. Date: Nov. 12, 2015

(65) Prior Publication Data
US 2017/0174605 A1 Jun. 22, 2017

(30) Foreign Application Priority Data
May 8, 2014 (EP) .................................... 14167588

(51) Int. Cl.
*B01D 3/38* (2006.01)
*C07C 51/44* (2006.01)

(52) U.S. Cl.
CPC .............. *C07C 51/445* (2013.01); *B01D 3/38* (2013.01)

(58) Field of Classification Search
CPC .............................. C07C 51/487; C07C 51/44
See application file for complete search history.

(56) References Cited

U.S. PATENT DOCUMENTS 2,352,253 A * 6/1944 Cockerille ............ C07C 51/487
562/898
5,306,398 A * 4/1994 Seidel ................... C07C 51/487
203/33

FOREIGN PATENT DOCUMENTS

DE        2423079 A1 * 11/1975
EP        0680810 A1 *  4/1995

* cited by examiner

*Primary Examiner* — Paul A Zucker
(74) *Attorney, Agent, or Firm* — Vorys, Sater, Seymour and Pease LLP

(57) ABSTRACT

Process for the recovery of carboxylic acid, in particular acetic acid containing carboxylic anhydride in particular-acetic anhydride and other impurities, which comprises: (a) treating a fraction, in particular a fraction originating from a wood treatment process, containing carboxylic acid and impurities with a metal salt in the presence of water, (b) treating at least part of the fraction obtained from step (a) to remove metal salt and, (c) treating at least part of the fraction obtained from step (b) by distillation, stripping or membrane separation to recover at least a purified carboxylic acid fraction.

21 Claims, No Drawings

PROCESS FOR THE RECOVERY OF CARBOXYLIC ACID AND WOOD TREATMENT PROCESS

This application claims priority to European application No. 14167588.4 the whole content of this application being incorporated herein by reference for all purposes.

The present invention concerns a process for the recovery of carboxylic acid, which is particularly useful to enhance the cost-efficiency of wood treatment processes using carboxylic acid derivatives such as in particular wood acetylation using acetic anhydride as acetylation reagent. Treated wood such as acetylated wood is useful e.g. as construction material presenting high service life and excellent resistance against environmental conditions and pathogens.

A wood acetylation process is described, for example, in EP 680810 whose relevant contents are incorporated by reference into the present patent application.

In order to enhance the efficiency and overall economics of treatment processes using carboxylic acid derivatives such as the aforesaid wood treatment process, the present invention now proposes a process for the recovery of carboxylic acid.

DE 2423079 C2 discloses a process for the recovery of acetic acid from waste acetic acid fractions containing acetic anhydride by hydrolysis of the acetic anhydride. The treated fraction is distilled in the presence of alkali metal salt.

The invention concerns a process for the recovery of carboxylic acid, in particular acetic acid containing carboxylic anhydride in particular acetic anhydride and other impurities, which comprises
(a) treating a fraction, in particular a fraction originating from a wood treatment process, containing carboxylic acid and impurities with a metal salt in the presence of water
(b) treating at least part of the fraction obtained from step (a) to remove metal salt and
(c) treating at least part of the fraction obtained from step (b) by distillation, stripping or membrane separation to recover at least a purified carboxylic acid fraction.

It has been found, surprisingly, that the process according to the invention allows for efficient recovery of carboxylic acid from waste carboxylic acid, in particular acetic acid, fractions. These fractions are often obtained by acetylation of polysaccharides, in particular from a wood acetylation process. The purified carboxylic acid can be isolated in substantially dry form. It is a useful starting material e.g. to produce acylating agents. The process according to the invention has also important advantages concerning process operation, e.g. by avoiding fouling of apparatus.

In the process according to the invention, the carboxylic acid is suitably selected from C1 to C6 alkyl carboxylic acids. Particular examples include propionic and, preferably, acetic acid.

In the present invention the carboxylic acid, in particular acetic acid, may in particular originate from industrial processes providing at least a carboxylic acid/carboxylic anhydride mixture such as for example acetylation of polysaccharides such as starch and wood treatment processes. Preferably, the carboxylic acid originates from a wood treatment process, in particular a wood acetylation process.

In a particular embodiment, the invention therefore further comprises recovering a carboxylic acid/carboxylic anhydride mixture containing other impurities from industrial processes, providing at least a carboxylic acid/carboxylic anhydride mixture, in particular a wood treatment process, and separating said mixture, preferably by distillation, into a first fraction consisting essentially of carboxylic anhydride, and optionally recycling said first fraction to an industrial process such as a wood treatment process, and a second fraction containing carboxylic acid, impurities, in particular impurities originating from wood, and carboxylic anhydride, and introducing at least part of said second fraction into step (a). If appropriate, the apparatus, in particular a distillation column, used in the process according to the invention comprise at least one part which is corrosion resistant for example made of enamel or glass, for example an enamel or glass coated steel part or other corrosion resistant materials such as titanium, Hastelloy® steel, copper, or polymer materials such as PTFE.

In the process according to the invention the metal salt is generally a non-halogenated salt. Often the metal salt is a basic salt, suitably selected from metal hydroxides, carbonates or carboxylates, in particular acetate. Preferably the metal salt is a non halogenated alkali salt. Potassium and sodium salts are preferred, sodium salts are more particularly preferred. Most preferably, the metal salt is selected from sodium carboxylate, in particular sodium acetate, sodium hydroxide and their mixtures.

In the process according to the invention the fraction introduced into step (a) often contains chlorinated compounds. Examples of chlorinated compounds include chloride salts, in particular NaCl, and chlorinated organic compounds such as acyl chlorides, in particular acetyl chloride. In this case the amount of metal salt supplied to step (a) is generally from 10 to 10000, preferably from 50 to 500 equivalents, more preferably from 80 to 200 equivalents relative to the molar amount of chlorine atoms contained in the chlorinated compounds contained in the fraction introduced into step (a).

In this aspect of the process according to the invention, the fraction introduced into step (a) generally contains an amount of chlorinated compounds corresponding to from 3 to 2000 ppm molar of chlorine atoms relative to the carboxylic acid, in particular acetic acid contained in said fraction. Often, the fraction introduced into step (a) contains equal to or more than 3 ppm molar of chlorine atoms relative to the carboxylic acid. Preferably, the fraction introduced into step (a) contains equal to or more than 4 ppm molar of chlorine atoms relative to the carboxylic acid. Most preferably, the fraction introduced into step (a) contains equal to or more than 5 ppm molar of chlorine atoms relative to the carboxylic acid. Often, the fraction introduced into step (a) contains equal to or less than 2000 ppm molar of chlorine atoms relative to the carboxylic acid. Preferably, the fraction introduced into step (a) contains equal to or less than 100 ppm molar of chlorine atoms relative to the carboxylic acid. Most preferably, the fraction introduced into step (a) contains equal to or less than 20 ppm molar of chlorine atoms relative to the carboxylic acid. The molar amount of chlorine atoms contained in the fraction introduced into step (a) can be suitably determined by the following method. Argentometric titration following the following protocol: 45 g of a fraction with around 10 ppm chloride was mixed with 120 ml of water, 10 ml 0.2% aqueous polyvinyl alcohol solution and 5 ml 2N $HNO_3$ and the titration performed by using a Methrom Titando 905 with Ag titrode, 0.01 N $AgNO_3$ as titrant at a dosage rate of 0.5 ml/min.

In the process according to the invention, the fraction introduced into step (a) generally contains impurities originating from wood.

For example, the fraction introduced into step (a) may contain inorganic impurities originating from wood. Salts, such as NaCl are an example of such impurities. The fraction introduced into step (a) may also contain organic impurities originating from wood. Terpenes and terpenoids are a particular example of organic impurities. Specific examples of terpenes and terpenoids include terpinenes, terpinolenes, α-terpineol acetate, α-fenchene, camphene, p-methyl isopropyl benzene (p-cymene), limonenes, α-fenchyl acetate, isobornyl acetate, α-pinene, β-pinene and pinocarvyl acetate.

The treatment of a fraction containing carboxylic acid and impurities with a metal salt in step (a) is carried out in the presence of water. The amount of water present in step (a) is related to the molar amount carboxylic acid anhydride contained in the carboxylic acid fraction. Typically, the water is added to the fraction prior to addition of the metal salt. Addition of a metal salt solution to the fraction, or addition of water to the fraction after the metal salt addition can also be carried out. Suitably, the molar amount of carboxylic acid anhydride contained in the carboxylic acid fraction is analyzed prior to step (a). Suitable analysis techniques are known to the person skilled in the art, e.g. gas chromatography. The amount of water present in step (a) is calculated accordingly. The amount of water present in step (a) generally is equal to or higher than 0.8 eq of the molar amount of carboxylic acid anhydride. More preferably, the amount of water present in step (a) is equal to or higher than 0.85 eq of the molar amount of carboxylic acid anhydride. Most preferably, the amount of water in the aqueous phase present in step (a) is equal to or higher than 0.9 eq of the molar amount of carboxylic acid anhydride. Often, the amount of water present in step (a) is equal to or lower than 1.2 eq of the molar amount of carboxylic acid anhydride. More preferably, the amount of water present in step (a) is equal to or lower than 1.15 eq of the molar amount of carboxylic acid anhydride. Most preferably, the amount of water present in step (a) is equal to or lower than 1.1 eq of the molar amount of carboxylic acid anhydride. In a most preferred aspect of this embodiment, the amount of water present in step (a) is from 0.95 to 1.05 eq of the molar amount of carboxylic acid anhydride. Addition of a controlled amount of water at this stage, avoiding too large an excess of water, allows for hydrolysis of residual carboxylic acid anhydride, while an efficient separation or essential reduction of salts and halogenated impurities from the fraction is possible. By the addition of a controlled amount of water in this step, fouling and/or corrosion of downstream apparatus can be avoided, which, especially in the case of fouling, is particularly advantageous when the process is run continuously. Another advantageous aspect is the avoidance of quality issues such as coloration of the end product. The scope of the term "water" is explained further below.

When the fraction introduced into step (a) contains organic impurities, in particular as described here before, in particular terpenes and terpenoids, the contents thereof is generally from 50 to 1500 ppm by weight preferably from 100 to 1000 ppm by weight more preferably from 300 to 700 ppm relative to the total weight of the fraction.

In the process according to the invention, the metal salt can be separated in step (b) by different techniques suitable for removal of a solid from a liquid phase such as filtration, precipitation, crystallization and, preferably, evaporation. In case the separation of metal salt is carried out by evaporation, the evaporation is preferably carried out in a forced flow evaporator, natural flow-evaporator, thermosiphon evaporator or a cattle evaporator. A natural flow-evaporator is preferred.

If appropriate, the evaporator is preferably made from corrosion resistant materials such as enamel or glass, for example an enamel or glass coated steel part or other corrosion resistant materials such as titanium, Hastelloy® steel, copper, or polymer materials such as PTFE, or materials lined or coated with at least one of the forgoing corrosion resistant materials.

In case the separation of metal salt is carried out by evaporation, the pressure thereof is typically from 10 mbar to 4 bar abs., preferably from 50 mbar to 1 bar abs., more particularly from 100 mbar to 500 mbar abs.

In case that the separation of metal salt is carried out by evaporation, the temperature at which the separation is carried out is typically the boiling temperature of the carboxylic acid containing fraction at the pressure indicated here before.

In case the separation of metal salt is carried out by evaporation, the process according to the invention generally comprises withdrawing a gas stream comprising carboxylic acid and impurities from said evaporation and feeding at least part of the gas stream into step (c). In that case the metal salt can be recovered either in solid form or in the form of a solution in carboxylic acid. The metal salt may suitably be recovered and recycled to step (a).

In a specific embodiment of the present invention, the metal salt, which is removed from the fraction obtained from step (a) in step b), is a solid and can be recovered by suitable methods, such as decantation, spinning, or, in particular, filtration. The metal salt which is recovered in solid form comprises generally the metal salt added in step a) or metal salt formed in step a) from impurities contained in the fraction fed to step a) and the metal salt added in step a). In particular, such salts formed in step a) may include alkaline metal chlorides, in particular NaCl. In one aspect, the fraction from which the metal salt is removed in solid form is cooled prior to removing the salt to enhance crystallization, and/or treated with seed crystals.

In another embodiment of the present invention, the metal salt is removed in step b) in the form of a liquid stream containing metal salt and carboxylic acid. Often, this liquid stream is the residue of the separation operation, in particular evaporation operation, performed in step b). In one aspect, the liquid stream is separated from any solids present in the liquid stream by decantation, spinning, or, in particular, filtration. Optionally, the liquid stream is cooled prior to the solid separation to enhance crystallization, and/or treated with seed crystals. Typically, the solids separated from the liquid stream are metal chlorides, in particular NaCl. Typically, the liquid stream, in particular after removal of the solids, is essentially free of chloride impurities. In one aspect of the present invention, the liquid stream, which typically contains carboxylic acid and the metal salt added in step a), is recycled into step a).

Step (c) is preferably a distillation carried out in a distillation column made at least in part from corrosion resistant materials such as discussed above.

In one embodiment, the fraction obtained by step b) is fed to step c) as a gas stream. Typically, the gas stream fed into step (c) is substantially free of metal salt.

In this embodiment, the gas stream fed into step (c) generally comprises less than 2 ppm wt. of halogen, in particular chloride. Preferably, the gas stream fed into step (c) comprises equal to or less than 1 ppm wt. % of halogen. More preferably, the gas stream fed into step (c) comprises equal to or less than 0.5 ppm wt. % of halogen. Most preferably, the gas stream fed into step (c) is substantially free of halogen, in particular chloride.

Alternatively, the gas stream obtained from the evaporation of step b) can be condensed and supplied subsequently, e.g. in liquid form to step c). In that case, the metal salt and halogen contents of the condensate are as described above for the gas stream in the case that the fraction obtained by step b) is introduced into step c) as a gaseous stream.

In the process according to the invention, in particular when acetic acid is recovered, step (c) is generally carried out at a pressure of from 0.01 to 4 bar abs., preferably from 0.05 to 1 bar abs., and more preferably from 100 mbar to 500 mbar abs., but at a lower absolute pressure than in step (b) to allow a vapor flow without intermediate compression.

When step (c) is a distillation, the latter is preferably carried out in a column having from 20 to 60 theoretical plates, more preferably from 30 to 40 theoretical plates.

In that case, if a gas stream is supplied from step (b) to the distillation of step (c), it is generally supplied at a level, from the bottom of the column, corresponding to from 60% to 90% of the total number of theoretical plates, preferably from 65% to 80% of the total number of theoretical plates of the column.

If a liquid stream is supplied from step (b) to the distillation of step (c), it is generally supplied at a level, from the bottom of the column, corresponding to from 60% to 90% of the total number of theoretical plates, preferably from 65% to 80% of the total number of theoretical plates of the column.

In step (c), it is generally preferred to withdraw purified carboxylic acid as, a side stream or as a bottom stream from the distillation; withdrawing the purified acid as a side stream is preferred. If the purified carboxylic acid is withdrawn as a side stream, the withdrawal generally is carried out at a level, from the bottom of the column, corresponding to from 0% to 20% of the total number of theoretical plates, preferably from 5% to 10% of the total number of theoretical plates of the column. In this case the use of a dividing wall column is preferred.

In a preferred embodiment of the invention, water is added to the fraction obtained by step (b) prior to step (c). This is particularly the case when the separation method in step (c) is distillation and/or stripping. Addition of water at this point allows for efficient reduction or substantial removal of remaining organic impurities, in particular terpenes and/or terpenoids in step (c). The amount of water added to the fraction obtained by step (b) generally is equal to or higher than 1 wt. %, calculated on the basis of total weight of fraction obtained by step (b). Preferably, the amount of water added to the fraction obtained by step (b) is equal to or higher than 3 wt. %. More preferably, the amount of water added to the fraction obtained by step (b) is equal to or higher than 5 wt. %. Most preferably, the amount of water added to the fraction obtained by step (b) is equal to or higher than 7 wt. %. Often, the amount of water added to the fraction obtained by step (b) is equal to or lower than 25 wt. %. Preferably, the amount of water added to the fraction obtained by step (b) is equal to or lower than 20 wt. %. More preferably, the amount of water added to the fraction obtained by step (b) is equal to or lower than 15 wt. %. Most preferably, the amount of water added to the fraction obtained by step (b) is equal to or lower than 12 wt. %. The water can be added to the fraction obtained by step (b) in a liquid form, or as steam. The term "water" denotes water of any quality (e.g. deionized water, purified water, distilled water, double-distilled water, filtered water, water from industrial processes or also municipal or city water, tap water, hard water, soft water), as well as an aqueous phase containing one or more metal salts and/or an aqueous phase further containing organic substances. In one aspect, water without salts or additional organic substances is preferred. In a another aspect of the invention, the water added to the fraction obtained by step (b) is recycled from the fraction distilled off in step (c). The distillate of step (c) generally contains water, carboxylic acid and organic impurities, which tend to separate into phases after condensation. The separated aqueous phase of the distillate can be recycled as "water", i.e. aqueous phase containing primarily water and carboxylic acid, to be added to the fraction obtained by step (b) before entering step (c). This efficiently reduces loss of carboxylic acid in the process. In another particularly preferred aspect, if step (c) employs distillation, the water is added to the fraction obtained by step (b) as steam or liquid into the distillation column below the feed point of the fraction obtained by step (b) into the column. If the water is added to the column as a liquid, most preferably, the water is directly added to the liquid distributor or re-distributor of the stripping section.

In a particular embodiment, the process according to the invention comprises (i) obtaining the fraction introduced into step (a) by distillation from a carboxylic acid/carboxylic acid anhydride mixture containing other impurities (ii) treating in step (b) at least part of the fraction obtained from step (a) by evaporation and (iii) treating a least part of the fraction obtained from step (b) by distillation.

In this embodiment, the heat demand for the evaporator employed, in step (ii), and/or the distillation column employed, in step (iii) can suitably be provided by the usage of energy supplied from the condenser of the distillation column in step (i).

The purified carboxylic acid obtained according to the present invention is generally substantially anhydrous, having for example a water content of from 1 to 5000 ppm wt. In the case that the fraction fed to step (a) is obtained from a wood acetylation process, optionally followed by further separation step as described in a particular embodiment above, where the fraction is submitted to a separation step providing a first and second fraction, the purified acid, in particular acetic acid, obtained by step (c), typically contains from 50 to 1500 ppm organic impurities originating from wood. The purified carboxylic acid, in particular acetic acid, can be suitably used to manufacture carboxylic anhydrides, e.g acetic anhydride. In one preferred aspect, the purified carboxylic acid may be reacted as absorption acid with a ketene to produce carboxylic anhydride. In another aspect, the purified carboxylic acid may be converted into a ketene which is reacted with carboxylic acid to produce carboxylic anhydride. The carboxylic anhydrides so obtained may be suitably used in the industrial processes contemplated above, in particular in a wood treatment process such as a wood acetylation process.

In a particular embodiment, the process according to the invention comprises (i) obtaining the fraction introduced into step (a) by distillation from a carboxylic acid/carboxylic acid anhydride mixture containing other impurities (ii) treating in step (b) at least part of the fraction obtained from step (a) by evaporation and (iii) treating a least part of the fraction obtained from step (b) by distillation.

The invention also concerns a process for the manufacture of treated wood, e.g. as disclosed in EP-A-0680810, in particular acetylated wood, which comprises the process for the recovery of carboxylic acid according to the invention.

The process according to the invention and its specific aspects and embodiments of the present invention can suitably be run batch-wise or continuously.

Should the disclosure of any patents, patent applications, and publications which are incorporated herein by reference conflict with the description of the present application to the extent that it may render a term unclear, the present description shall take precedence.

The examples here after are intended to illustrate the invention without however limiting it.

EXAMPLE

A continuous flow of a fraction containing carboxylic acid and impurities, which is liquid effluent from a wood acetylation process, containing 50 wt. % acetic acid, 49 wt. % acetic anhydride and 1 wt. % of terpenes, terpene derived impurities and other organic impurities is submitted to a first distillation, employing a distillation column made of titanium.

This distillation column is equipped with structured packing which equals 20 theoretical stages. The chosen reflux ratio is 3. The column is operated at an pressure of 0.5 bar abs. at the top of the column. From this first distillation column a condensed stream is withdrawn at 93.6° C. with an acetic acid content of 98 wt. %, 20 ppm of chlorine (expressed as chlorine atoms) and the remaining rest is acetic anhydride, terpenes and terpenoids.

As step (a), in an intermediate treatment vessel, the top product of the first distillation is treated with a small amount of water in order to react with the remaining acetic anhydride. To the same intermediate treatment vessel, a flow of a 50% NaOH solution in water is added to the fraction obtained to provide 200 molar equivalents Na+ relative to the molar amount of chlorine atoms contained in the chlorinated compounds of the top product of the first distillation. The flowrates of water and NaOH solution to the intermediate vessel are calculated such that the water content reaction mixture is 1.05 eq relative to the content of acetic anhydride while maintaining the appropriate amount of NaOH.

In a step (b), the fraction obtained by step (a) is fed into a natural flow evaporator which is operated at a pressure of 0.3 bar abs. The fraction obtained by step (b) is substantially free of halogen, in particular chloride.

A small side stream of 0.5 wt. % of the liquid evaporation residue is withdrawn from the evaporator, cooled down to 30° C. and passed over a filter. Since the formed NaCl is basically indissoluble in acetic acid at low water concentration, it is removed as a precipitated salt by the filtration step. The dissolved Na-Acetate passes the filter and is recycled to the intermediate treatment vessel in which step (a) is performed.

The water content of the vapor fraction obtained by step (b) is further increased up to 10 wt % and submitted to step (c).

To perform step (c), the fraction obtained by step (b) and enriched with water is fed as vapor stream into a distillation column, This distillation column is equipped with structured packing which equals 35 theoretical stages. The chosen reflux ratio is 5. The column is operated at a pressure of 0.2 bar abs. at the top of the column.

From this distillation column a condensed overhead stream is withdrawn at 60.3° C. with a water content of 95%. wt. This stream contains more than 80% of all terpenes, terpene derived impurities and other organic impurities which were contained in the fraction fed to step (c).

The acetic acid, withdrawn at the bottom of the column of step (c) with a concentration of 99.5%, is substantially free of halogen, in particular chloride, containing less than 20% of all terpene and other organic impurities which were contained in the fraction fed to step (c).

The material is stored in a stainless steel vessel and has the corrosiveness of pure acetic acid. No coloration of the product is observed over time.

The invention claimed is:

1. A process for recovery of carboxylic acid from a mixture, the process comprising:
providing a carboxylic acid mixture comprising a C1-C6 alkyl carboxylic acid, a carboxylic anhydride and impurities originating from wood;
treating the carboxylic acid mixture with a first metal salt in the presence of water to form a first treated mixture;
removing a salt stream comprising the first metal salt, a second metal salt, or a combination thereof from at least a part of the first treated mixture to form a second treated mixture, the second metal salt being formed from a reaction between the impurities and the first metal salt; and
fractionating at least a part of the second treated mixture by distilling, stripping or membrane separating to recover at least a purified carboxylic acid fraction.

2. The process according to claim 1, wherein the first metal salt is an alkali salt.

3. The process according to claim 1, wherein the carboxylic acid mixture contains chlorinated compounds corresponding to from 3 to 2000 ppm molar equivalents of chlorine atoms relative to the carboxylic acid.

4. The process according to claim 3, wherein the amount of the first metal salt is from 10 to 10000 equivalents relative to the molar amount of chlorine atoms contained in the chlorinated compounds.

5. The process according to claim 1, wherein the carboxylic acid mixture contains terpenes, terpenoids, and mixtures thereof.

6. The process according to claim 5, wherein the carboxylic acid mixture contains from 50 to 1500 ppm by weight of the terpenes, terpenoids, and mixtures thereof.

7. The process according to claim 1, wherein an amount of water present when forming the first treated mixture is from 0.8 to 1.2 molar equivalents relative to the amount of the carboxylic acid anhydride present in the carboxylic acid mixture.

8. The process according to claim 1, wherein the salt stream is removed by evaporation of the first treated mixture.

9. The process according to claim 1, wherein the salt stream is removed as a solid from the first treated mixture, and/or as an evaporation residue obtained from the first treated mixture, and/or as a liquid stream obtained from the evaporation residue.

10. The process according to claim 8, further comprising:
withdrawing a gas stream comprising the C1-C6 alkyl carboxylic acid and the impurities from the evaporation of the first treated mixture, the gas stream comprising less than 1 ppm wt. % of halogen;
wherein the gas stream comprises at least a part of the second treated mixture that is fractionated.

11. The process according to claim 1, further comprising:
adding water to the second treated mixture prior to fractionating.

12. The process according to claim 11, wherein the amount of water added to the second treated mixture is from 1 to 25 wt. % relative to the total mass of the second treated mixture that is fractionated.

13. The process according to claim 1, wherein the second treated mixture is fractionated by distillation and the purified carboxylic acid fraction is obtained as a side stream or a bottom stream.

14. The process according to claim 1, further comprising:
recovering a carboxylic acid/carboxylic anhydride mixture containing impurities from a wood treatment process;
separating a portion of the carboxylic anhydride from the carboxylic acid/carboxylic anhydride mixture as a first fraction;
optionally recycling the first fraction to the wood treatment process; and
separating the carboxylic acid mixture from the carboxylic acid/carboxylic anhydride mixture as a second fraction.

15. A process for manufacturing treated wood comprising:
performing a wood treatment process with a carboxylic anhydride;
obtaining a carboxylic acid mixture comprising a C1-C6 alkyl carboxylic acid, the carboxylic anhydride and impurities from the wood treatment process;
treating the carboxylic acid mixture with a first metal salt in the presence of water to form a first treated mixture;
removing a salt stream comprising the first metal salt, a second metal salt, or a combination thereof from at least a part of the first treated mixture to form a second treated mixture, the second metal salt being formed from a reaction between the impurities and the first metal salt; and
fractionating at least a part of the second treated mixture by distilling, stripping or membrane separating to recover at least a purified carboxylic acid fraction.

16. The process according to claim 1, wherein the C1-C6 alkyl carboxylic acid is acetic acid and the carboxylic anhydride is acetic anhydride.

17. The process according to claim 2, wherein the first metal salt is sodium acetate.

18. The process according to claim 12, wherein the amount of water added to the second treated mixture is from 7 wt. % to 12 wt. %.

19. The process according to claim 17, wherein the sodium acetate is formed by adding sodium hydroxide to the carboxylic acid mixture.

20. The process according to claim 1, further comprising:
recovering the salt stream; and
recycling the salt stream to a portion of the carboxylic acid mixture.

21. The process of claim 1, wherein the second treated mixture is fractionated by distillation;
wherein the impurities are obtained as an overhead stream, and wherein the purified carboxylic acid fraction is obtained as a side stream or a bottom stream.

* * * * *